United States Patent [19]

Iinuma

[11] Patent Number: 5,450,850
[45] Date of Patent: Sep. 19, 1995

[54] SYSTEM FOR EXAMINING CARDIAC FUNCTION

[75] Inventor: Kazuhiro Iinuma, Tochigi, Japan

[73] Assignee: Kabushiki Kaisha Toshiba, Kanagawa, Japan

[21] Appl. No.: 336,081

[22] Filed: Nov. 7, 1994

[30] Foreign Application Priority Data

Nov. 5, 1993 [JP] Japan ................................. 5-276835

[51] Int. Cl.⁶ .............................................. A61B 8/00
[52] U.S. Cl. ............................ 128/661.09; 128/672; 128/713
[58] Field of Search ...................... 128/661.04, 661.08, 128/661.09, 661.10, 691, 672, 670, 675, 713, 662.01

[56] References Cited

U.S. PATENT DOCUMENTS 4,796,634  1/1989  Huntsman et al. .............. 128/662.01
5,086,776  2/1992  Fowler et al. ................... 128/661.09

*Primary Examiner*—George Manuel
*Attorney, Agent, or Firm*—Finnegan, Henderson, Farabow, Garrett & Dunner

[57] ABSTRACT

The minimum amount of data regarding cardiac function required for evaluation is measured non-invasively and various cardiac function parameters are computed (estimated) based on the measured values, and the results are displayed in an optimal form for evaluation. A cardiac function examination system comprises a device for measuring the amount of blood ejected from the ventricle to the aorta based on reflected ultrasonic pulses, a device for measuring the aorta or thick artery diameter based on reflected ultrasonic pulses, a device for inputting at least one of maximum and minimum blood pressure values, a device for computing a maximum ventricular volume or an ejection fraction, and a device for acquiring parameters such as cardiac volume or aorta pressure parameter regarding cardiac function based on the measured values of the ejection amount, the blood vessel diameter, and the ejection fraction, or any one of these, and the input pressure values.

23 Claims, 14 Drawing Sheets

SYSTEM FOR EXAMINING CARDIAC FUNCTION

BACKGROUND OF THE INVENTION

The present invention relates to a system for examining a cardiac function suitable for medical examination, and in particular suitable for examining, diagnosing, and monitoring heart pumping (cardiac function).

The human heart, which is responsible for pumping blood throughout the whole body, is one of the most important organs a subject. In recent years, in preventing and curing cardiac diseases, it has been necessary to make an overall evaluation of the pumping function of the heart (hereinafter referred to as cardiac function).

Overall evaluation of cardiac function is made based on intercardiac pressure, cardiac volume, ejection discharge, and a quantity which represents the time change thereof. Hitherto, several methods have been attempted to obtain the individual parameters thereof. However, an overall evaluation of cardiac function can only be made using examination data collected by employing appropriate modalities to analyze the individual parameters mentioned above, artificially studying the results of the analysis, and then making a diagnosis of the study.

In conventional cardiac function examinations, a modality which places a burden (or invasive) on the patient has been frequently used to gather examination data. As a result of this, the patient experiences a feeling of uncertainty and serious mental problems, so that he cannot readily go through the examination. In the same way, the examiner also is seriously burdened because he must be extremely careful not to put stress on the patient during examination and careful in operating the system.

In making an overall evaluation of cardiac function, a large number of parameters have to be individually analyzed. A portion of them can certainly be automatically analyzed, but it takes a long time and a lot of trouble to obtain all of the parameters. In particular, this tendency is stronger when a plurality of modalities is used. In addition, many people are required to carried out the individual parameter analysis. Further, the results of analysis are not necessarily in a suitable form for the overall evaluation of cardiac function, so that a long period of time is required to make the overall evaluation.

SUMMARY OF THE INVENTION

In view of the above-described problems of the prior art, the present invention aims at providing a cardiac examination system which, without seriously burdening (or invading) the patient, allows examination data necessary for an overall evaluation of the cardiac function to be obtained readily within a short time, and based on this data to provide parameters in a form useful for an overall evaluation, diagnosis, and monitoring of the cardiac function.

To these ends, there is provided according to the present invention a cardiac function examination system, as shown in FIG. 1, whose critical portion includes ejection measuring means for measuring the blood flow from the ventricle to the aorta using information based on ultrasonic pulse reflection, blood vessel diameter measuring means for measuring the diameter of the aforementioned aorta or thick artery using information based on ultrasonic pulse reflection, blood pressure input means for inputting at least one of maximum or minimum blood pressure value, and parameter acquiring means for acquiring parameters regarding cardiac function based on the measured values of the ejection measuring means, the blood vessel diameter measuring means and the input value of the blood pressure input means.

In particular, the critical portion is defined as the portion comprising the aforementioned ejection amount measuring means with ejection fraction measuring means for measuring maximum volume or ejection fraction of the left ventricle of the heart added thereto, and parameter acquiring means for acquiring parameters regarding cardiac function based on the measured values of the blood vessel diameter measuring means and the ejection fraction measuring means and the input value of the blood pressure input means.

According to another aspect of the present invention, there is provided a cardiac function examination system comprising blood vessel diameter measuring means for measuring the diameter of the aorta or the thick artery using information based on ultrasonic pulse reflection, blood pressure input means for inputting maximum or minimum blood pressure value, and parameter acquiring means for determining and outputting parameters regarding changes of absolute values of the aorta pressure or blood pressure which occur with time based on the measured value of the blood vessel diameter measuring means and the input value of the blood pressure input means.

According to still another aspect of the present invention, there is provided a cardiac function examination system comprising ejection measuring means for measuring the blood flow from the ventricle to the aorta using information based on ultrasonic pulse reflection, ejection fraction measuring means for measuring the ejection fraction or maximum volume of the left ventricle using information based on ultrasonic pulse reflection, and parameter acquiring means for determining and outputting parameters regarding cardiac volume absolute values and how these change with time from information based on measured value of the ejection measuring means and the ejection fraction measuring means.

Information based on ultrasonic pulse reflection is used to measure blood flow from the ventricle to the aorta. The information based on ultrasonic pulse reflection is also used to measure the diameter of the aorta or thick artery. At least one of the maximum or minimum blood pressure value is input. The ejection fraction or the maximum ventricular volume is measured depending on the circumstances. Based on these data, there are computed parameters regarding cardiac function (such as changes of blood pressure of the aorta or thick artery with time, changes between the blood pressure of the aorta or thick artery and volume of the left ventricle with time, amount of work done by the left ventricle, pressure rise ratio from the time the R-wave appears on the cardiogram to the time of pressure rise of the aorta or thick artery, etc.). These parameters are shown with, for example, the horizontal axis defined as the time axis and cardiac time phase matched.

In this way, first, the minimum basic data required, which comprises a portion of the information regarding cardiac function, is obtained non-invasively. Then, this basic data is used to compute the other parameters regarding cardiac function which also comprise a part of the information regarding cardiac function. Examination data is provided in a form suitable for making an overall evaluation of cardiac function by, for example, displaying the desired plurality of parameters among the computed parameters with the heart time phases matched. An esophagus insertable ultrasonic probe including two pairs of simultaneously drivable transducers may be used to simultaneously measure the ejection and the blood vessel diameter, both of which are basic data, so that data processing can be carried out easily.

In another aspect of the invention, changes in the absolute value of the aorta pressure or blood pressure with time can be obtained from the blood vessel diameter and the maximum and minimum blood pressure value. In addition, the absolute value of the cardiac output and changes thereof with time can be obtained from the blood flow and the ejection fraction or the maximum ventricular volume. Accordingly, the parameters which represent cardiac function can be further computed and displayed in diversified ways, thereby perfecting the examination function.

BRIEF DESCRIPTION OF THE DRAWINGS

For a more complete understanding of the present invention, reference will be made to the following detailed explanations in conjunction with the accompanying drawings in which.

DESCRIPTION OF PREFERRED EMBODIMENTS

There will be hereunder described one embodiment of the ultrasonic cardiac function examination system using ultrasonic pulse signals with reference to FIGS. 1 through 14. In this embodiment, various information regarding cardiac function is obtained. This information includes information represented by directly measured basic data and parameters calculated (estimated) from the basic data.

Figure 1:
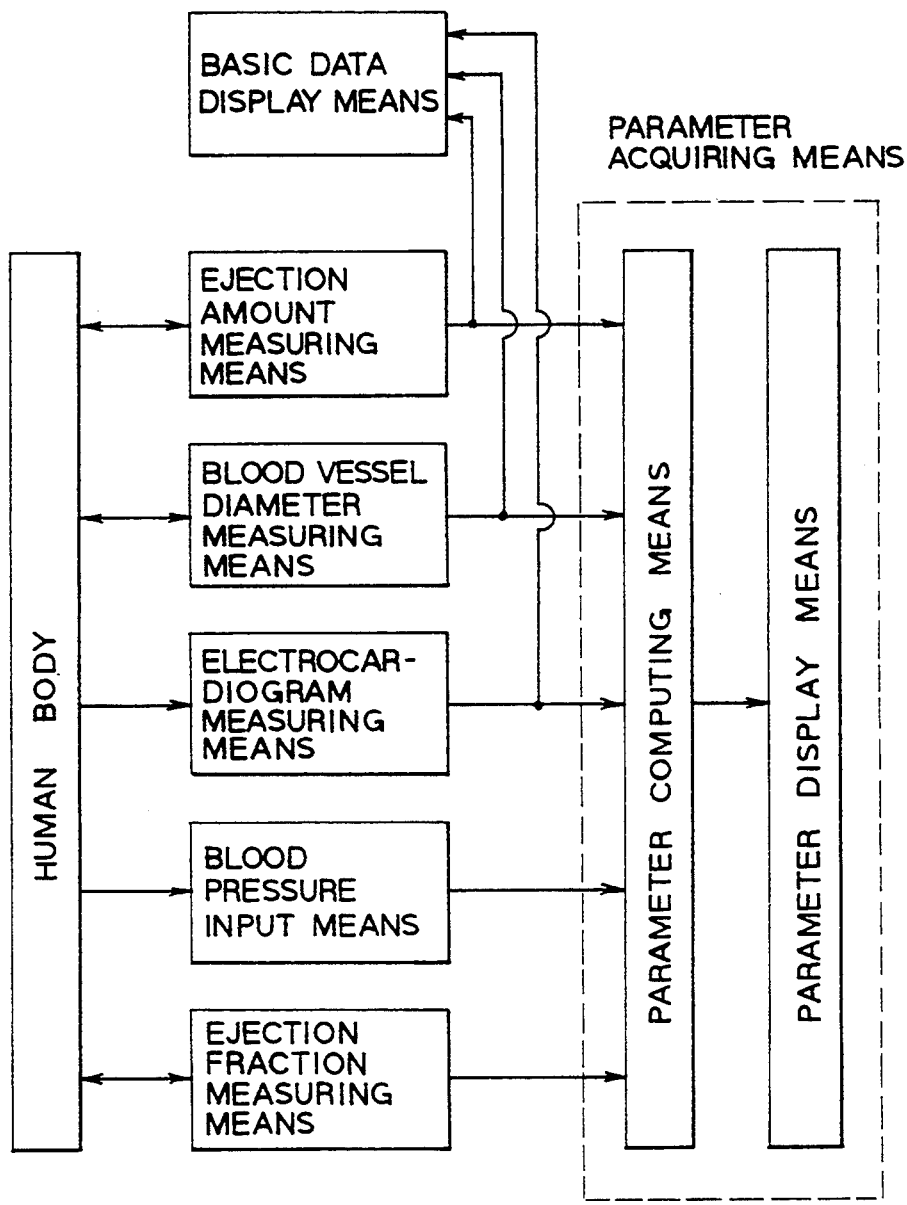
FIG. 1 illustrates a functionally-composed ultrasonic cardiac function examination system of one embodiment according to the invention.

First, FIG. 1 shows a functionally-composed ultrasonic cardiac function examination system, which will be described in detail in the following FIGS. 2 to 14 using practical components.

Figure 2:
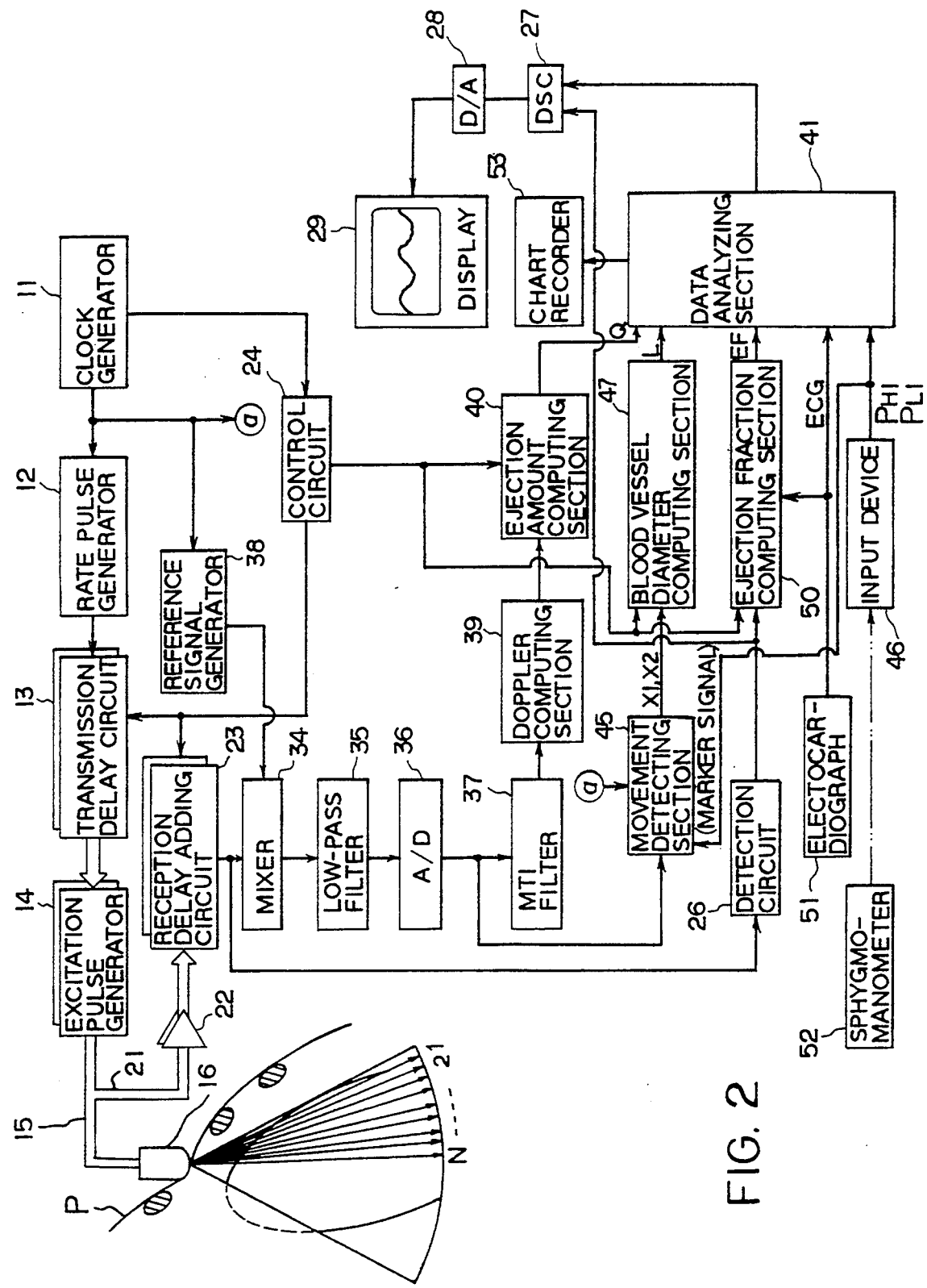
FIG. 2 is a detailed block diagram of the ultrasonic cardiac function examination system illustrated in FIG. 1.

An ultrasonic cardiac function examination system shown in FIG. 2 comprises a clock generator 11 for generating a fundamental clock signal having, for example, a frequency of 40 MHz, which are supplied to a rate pulse generator 12. Based on the fundamental clock signal, the rate pulse generator 12 generates a rate pulse of, for example, 5 kHz, which is supplied to a transmission delay circuit 13. The transmission delay circuit 13 causes the rate pulse to be delayed in accordance with a delay time pattern based on a delay control signal (not shown). Then, it causes a plurality of channel delay pulse signals to be generated corresponding to the number of oscillators (described later). These pulse signals are sent to an excitation pulse generator 14 of the next stage. This excitation pulse generator 14 has a plurality of pulsers for generating high voltage excitation pulses corresponding to the plurality of delay pulse signals. Therefore, each of the excitation pulses has a commanded delay time.

The output end of the excitation pulse generator 14 is connected to an ultrasonic probe 16 through a signal line 15. In the embodiment, the ultrasonic probe 16 is a sector electronic probe having a plurality of piezoelectric transducers which are arranged into an array. Application of excitation pulses to each of the piezoelectric transducers causes ultrasonic pulses to be sent. When the ultrasonic pulses are reflected and received from the subject P, they are converted into electric pulse echo signals.

The ultrasonic probe 16 is also connected to a preamplifier 22 through a signal line 21 as illustrated in FIG. 2. The preamplifier has a plurality of amplification circuits incorporated therein in accordance with the number of transducers. They amplify the amplitude of the echo signals sent from the ultrasonic probe 16. The amplified echo signals are sent to a receiving delay adding circuit 23 of the next stage and are delayed and added thereat. A control circuit 24 is capable of controlling the transmission and reception delay time pattern.

The output of the receiving delay adding circuit 23 is connected to a DSC (digital scan converter) 27 through a detection circuit 26 for obtaining a B-mode image signal. The DSC 27 receives basic data representing cardiac function (described later) and various parameters computed (estimated) from the basic data. The DSC 27 converts this input data to frame image data in a commanded display format. This image data converted by the DSC 27 is called out via a D/A converter 28 every predetermined time. Then, it is displayed on a TV monitor 29.

The output of the aforementioned receiving delay adding circuit 23 is also connected to an MTI filter 37 through a mixer 34, low-pass filter 35, and an A/D converter 36. Of these components, the mixer 34 and the low-pass filter 35 perform phase detection. The mixer 34 multiplies a reference signal of, for example, 2.5 MHz, supplied from a reference signal generator 38, and the output signal of the receiving delay adding circuit 23. The resultant signal is filtered through the output side of the low-pass filter 35 and the filtered signal is converted into a digital signal by the A/D converter 36. The circuit extending from the mixer 34 to the MTI filter 37 is actually formed into two lines for providing a forward or reverse path for blood flow Doppler signals from the echo signals. The aforementioned reference signal generator 38 receives reference clock signals from the clock generator 11 to form two reference signals having a phase difference of exactly 90°. These signals are supplied to the mixer 24.

The MTI filter 37 is a filter for removing wave components reflected from, for example, parts which move slowly such as the cardiac muscle. The output end of the MTI filter 37 is connected to an ejection amount computing section 40 through a Doppler computing section 39 for computing the Doppler shift frequency $f_d$. This allows the Doppler shift frequency $f_d$ computed by the Doppler computing section 39 to be sent to the ejection amount computing section 40.

In the ejection amount computing section 40, sector scanning lines extending the same distance from the body surface or the Doppler shift frequency $f_d$ value for every predetermined length of time from the rate pulse time are used to compute how much blood has flowed from the left ventricle to the aorta. More specifically, it is done as follows in a known manner. After the ultrasonic probe 16 is placed against the chest surface and a plurality of ultrasonic beams are sent within the cross section of the left ventricle outflow path, the blood flow is measured from the reflected Doppler signal at the point of intersection of the line which transverses the ultrasonic beam and the reflected ultrasonic beam (i.e., ultrasonic pulse Doppler method). Then, each annular cross sectional area is multiplied by each of a plurality of blood flow speeds (Doppler shift frequencies) at the plurality of intersections, thus obtained, and the results are added together (i.e., cardiac flow measuring method). This method of measurement allows 60 instantaneous cardiac output points (ejection amount) at 60 points to be computed per second, for example, every 16.7 msec in real time.

The calculated data of the ejection amount computing section 40 is supplied to a data analyzing section 41.

The converted phase detection output produced by the A/D converter 36 is also supplied to a movement detection section 45. The movement detection section 45 is constructed, in a known manner. It includes an amplitude detection circuit, a phase detection circuit, a phase difference circuit, a phase distance converting circuit, a sample point specifying circuit, a mixer, etc. A marker signal for specifying an initial sample point is supplied to the sample point specifying circuit of the movement detection section 45 by means of an input device 46 such as a keyboard or a mouse. This allows the points of intersection of the ultrasonic beam, which passes through the center of the blood vessel, and the blood vessel wall to serve as two sample points in a cross sectional blood vessel image (moving cross sectional image) to be obtained from ultrasonic pulses which were transmitted to the aorta or thick artery (for example, the brachial artery) (hereinafter referred to as "aorta, etc.") to the ultrasonic probe 16. The sample point positions and position changes with time are automatically traced to compute data X1 and X2 regarding position changes of the two sample points with time in real time.

The position data X1 and X2 of the two sample points computed by the movement detection section 45 are successively sent to a following blood vessel diameter computing section 47. Based on the position data X1 and X2 of the sample points, the blood vessel diameter computing section 47 computes "X2-X1" to automatically obtain in real time the blood vessel diameter. The sampling based on the ultrasonic beam can be carried out quickly enough. For example, computation of the blood vessel diameter can be easily carried out at, for example, the same interval in which the instantaneous cardiac output is computed, or 16.7 msec. It is possible to obtain data which can be used to obtain a virtually continuous curve in terms of time. Since the aforementioned movement detection section 45 determines the sample points by the phase information based on ultrasonic reflected wave, it is capable of computing an accuracy in the order of a fraction of the ultrasonic wavelength (for example, at 5 MHz, the wavelength is 0.3 mm), or to several tens of $\mu$m to several hundreds of $\mu$m. The computed result is sent to the data analyzing section 41.

The output side of the aforementioned detection circuit 26 for obtaining a B-mode image has also connected thereto an ejection fraction computing section 50. An ECG signal from an electrocardiograph 51 is supplied to the ejection rate computing section 50. Based on the minor axis lengths Rs and Rd at end sistole and end diastole respectively obtained from the left ventricle minor axis image or minor axis cross section image data by ultrasonic pulses, the ejection fraction computing section 50 computes the ejection fraction EF of a spot using the following formula:

$$EF=[(Rd-Rs)/Rd]^n,$$

where n nearly equals 2. The ejection fraction EF is the ratio of ejection amount SV to the cardiac volume in the end diastole. For convenience, as described above, the minor axis ratio can be computed to easily obtain an ejection fraction EF of high reproducibility. The spot data regarding ejection fraction EF is supplied to the data analyzing section 41. Of course, end diastolic ventricular volume $V_m$, obtained from an ultrasonic B-mode image can be used instead of EF.

The ECG signal output from the aforementioned electrocardiograph 51 is sent to the data analyzing section 41 to match the timing in data processing and display, described later.

The on and off operation of each of the aforementioned ejection amount computing section 40, the blood vessel diameter computing section 47, and the ejection fraction computing section 50 is controlled by the control section 24 based on the measuring procedure taken by the operator. For example, since in most cases the ejection fraction computing section 50 only needs to be operated once at the beginning, when the ejection fraction is being measured, the ejection amount computing section 40 and the blood vessel diameter computing section 47 are turned off. The ejection amount computing section 40 and the blood vessel diameter computing section 47 only need to turned on when the ejection amount and the blood vessel diameter are being measured respectively.

Further, the examination system of the embodiment includes a sphygmomanometer 52 which uses cuffs as a non-invasive measuring means to avoid burdening the patient whose maximum and minimum blood pressures are being measured. The measured maximum blood pressure $P_{H1}$ and minimum blood pressure $P_{L1}$ are input to the data analyzing section 41 by manually operating the input device 46. A pressure catheter may be used for the sphygmomanometer.

The data analyzing section 41 includes a computer for matching the timing of the input basic data regarding cardiac function and for displaying this result, and for computing and displaying the parameters of the cardiac function. The data analyzed by the data analyzing section 41 is displayed on the TV monitor 29 through the DSC 27 and can be recording on a recorder 53, when necessary.

Next, the operation of the embodiment, illustrating different aspects, will be described mainly with reference to the processing of the data analyzing section 41.

First, basic data collection and display thereof for cardiac function evaluation will be described with reference to FIGS. 3 through 6.

Figure 3:
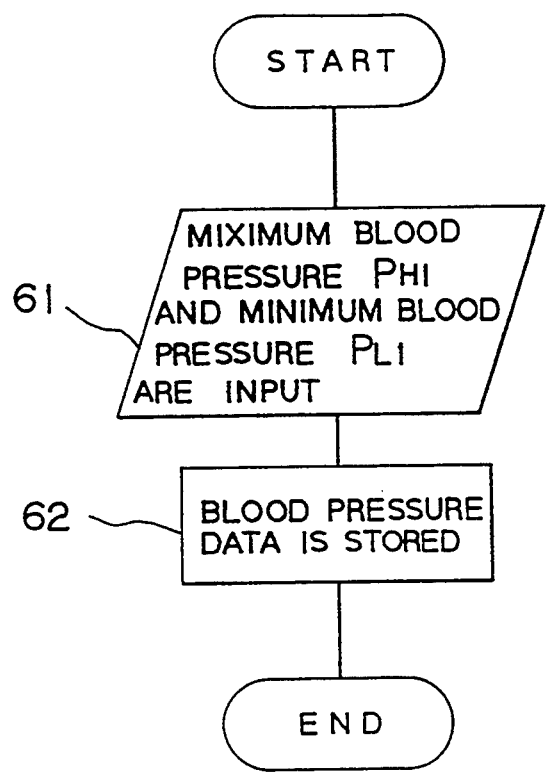
FIG. 3 is a flow chart illustrating an example of the process of incorporating blood pressure data by manual input of a sphygmomanometer.

Blood pressures of the patient are measured using the sphygmomanometer. To input these measured values to the data analyzing section 41, a procedure program shown in FIG. 3 is started. The maximum blood pressure $P_{H1}$ and minimum blood pressure $P_{L1}$ manually input through the input device 46 are read into the data analyzing section 41 (Step 60) to store this data in a predetermined memory area (Step 61).

In measuring the ejection fraction EF or maximum ventricular volume $V_m$, the ultrasonic probe 16 is positioned against the body surface to obtain a cardiac minor axis or long axis B-mode image so that ultrasonic pulses are transmitted from and returned to the probe. At the same time, the control circuit 24 causes the ejection fraction computing section 50 to operate. The ejection fraction computing section 50 has supplied thereto a usable ejection fraction EF or maximum ventricular volume $V_M$ which can be readily obtained, as mentioned above, from the minor axis or long axis image. Along with this, the data analyzing section 41 allows the procedure, illustrated in FIG. 4, to be started. The data analyzing section reads in the supplied ejection fraction EF (Step 71) to store this data into a predetermined memory area (Step 72).

The aorta diameter L as blood vessel diameter and the ejection amount Q are measured for display. Here, the data analyzing section 41 starts the program illustrated in FIG. 5, After the control circuit 24 has caused the blood vessel diameter computing section 47 to operate, ultrasonic pulses are transmitted to the chest surface, which are reflected back to the ultrasonic probe 16. As described above, this allows the blood vessel diameter computing section 47 to compute the aorta diameter L virtually in real time. This diameter data is supplied to the data analyzing section 41. The data analyzing section 41 reads in the diameter L data supplied as well as the ECG signal supplied from the electrocardiograph (Step 81) for a plurality of heart beats. This read in data are stored in a predetermined memory area (Step 82).

After the ejection amount computing section 40 has been operated by a command from the control circuit 24, ultrasonic pulses are transmitted from the ultrasonic probe 16 and reflected back thereto. As described above, this allows the ejection amount computing section 40 to compute the ejection amount (instantaneous ejection volume) Q (l/min.) virtually in real time. This ejection amount data is supplied to the data analyzing section 41. The data analyzing section 41 reads in the ejection amount Q supplied as well as the ECG signal supplied from the electrocardiograph (Step 83) for a plurality of heart beats. This read in data is stored in a predetermined memory area (Step 84).

Next, the aorta diameters L and the ejection amounts Q for the aforementioned plurality of heart beats are averaged to obtain the diameter L and the ejection amount Q data for one heart beat or a plurality of heart beats (Step 85). Then, timing matching is carried out for the waveforms, based on the ECG signals which have been read in Steps 81 and 83, of the data regarding the aorta diameter L, the ejection amount Q, and the electrocardiogram data. This data is output to the DSC 27 and the recorder 53 (Step 86). Accordingly, as shown in FIG. 6, with the time as the horizontal axis, the aorta diameter and the ejection amount can be displayed for one or plurality of heart beats, while the cardiac timings of the aorta diameter L, the ejection amount Q, and the electrocardiogram are matched.

Figure 6:
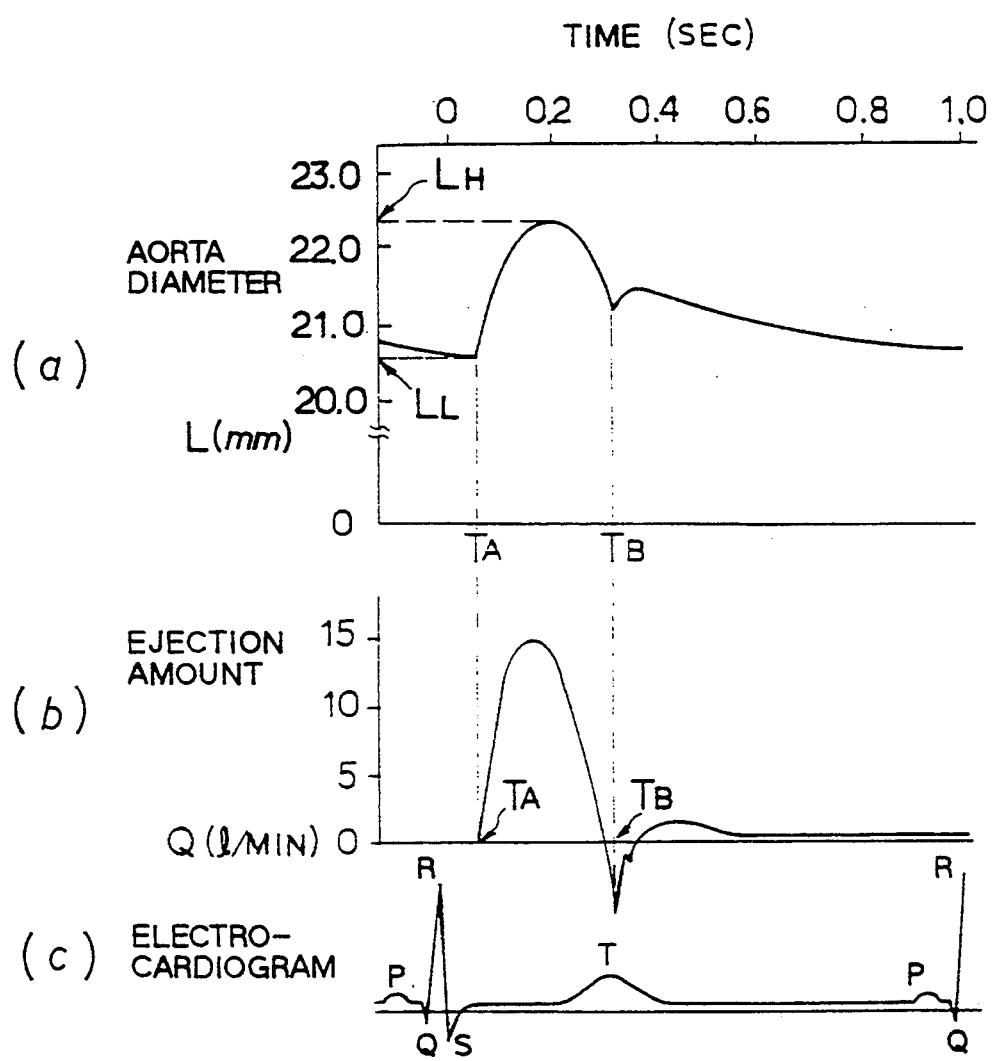
FIG. 6 shows graphs each illustrating respectively how the diameter of the aorta, the blood flow, and the electrocardiogram waveform changes with time.

FIG. 6 illustrates the data for one heart beat. FIG. 6(a) is an enlarged view of the aorta diameter L waveform which changes with time, while FIG. 6(b) shows the waveform of the ejection amount Q. The ejection amount waveform shows that when the left ventricle is filled with blood and contracts, its pressure rises. When the pressure exceeds the aorta pressure at time $T_A$ (opening-start time), the aortic valve opens and blood is discharged from the ventricle to the aorta. When the ventricle moves at time $T_B$ (closing time) from its systole (contraction period) to diastole (expansion period), the aortic valve closes so that no blood is ejected, with some blood flowing in the reverse direction.

Then, based on the collected basic data as described above, there will be described the computation and display of a parameter for cardiac evaluation.

While the aorta diameter can be displayed as shown in FIG. 6(a), the aorta pressure is an important parameter in evaluating cardiac function. From physiological studies, it is known that variations in this pressure is proportional to changes in the blood vessel diameter. Therefore, with the aortic pressure defined as P, the maximum blood pressure $P_H$, the minimum blood pressure $P_L$, the aorta diameter L, maximum diameter $L_H$ of the aorta, and minimum diameter $L_L$ of the aorta, it can be shown that aortic pressure changes in proportion to changes in aortic diameter by the following formula:

$$(P-P_L)/(P_H-P_L)=(L-L_L)/(L_H-L_L) \quad (1)$$

From (1), the following expression is established:

$$P=P_L+(P_H-P_L).(L-L_L)/(L_H-L_L) \quad (2)$$

$L_H$ and $L_L$ is determined from the measured aortic diameter value.

Generally speaking, of the maximum blood pressure $P_{H1}$ and minimum blood pressure $P_{L1}$ measured by the sphygmomanometer having cuffs, the maximum blood pressure $P_{H1}$ is made a little larger than the true value $P_H$, while the minimum blood pressure $P_{L1}$ is made a little smaller than the true value $P_L$. Therefore, using the correction factors $\alpha_1$ and $\beta_1$, the following formula is established from (2), where $\alpha_1$ and $\beta_1$ are small values of 5% or less:

$$P=(1+\alpha_1)P_{L1}+\{(1-\beta_1)P_{H1}-(1+\alpha_1)P_{L1}\}\cdot(L-L_L)/(L_H-L_L) \quad (3)$$

When $$\alpha=\alpha_1\approx\beta_1 \quad (4),$$

then (3) becomes:

$$P=(1+\alpha)P_{L1}+\{(P_{H1}-P_{L1})-\alpha(P_{H1}+P_{L1})\}\cdot(L-L_L)/(L_H-L_L) \quad (5)$$

When an appropriate value between 1 and 5% is selected for the aortic pressure P can be obtained from (5).

Since $\alpha$ is a small value, $\alpha=0$. Substituting $P_{H1}$ and $P_{L1}$ for $P_H$ and $P_L$ respectively in (2) gives:

$$P=P_{L1}+(P_{H1}-P_{L1})\cdot(L-L_L)/(L_H-L_L) \quad (6)$$

This expression may be satisfactorily used for practical purposes as an approximation.

Figure 5:
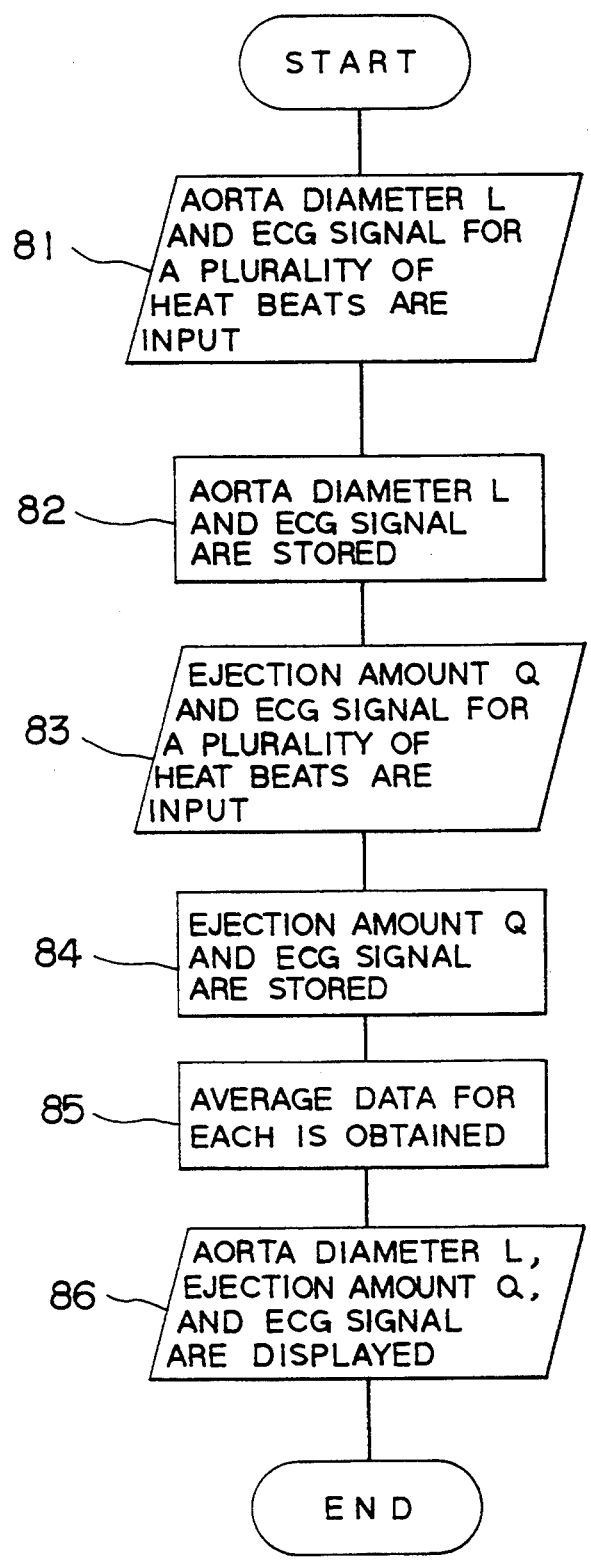
FIG. 5 is a flow chart illustrating an example of the process of incorporating blood flow and the aorta diameter.
Figure 7:
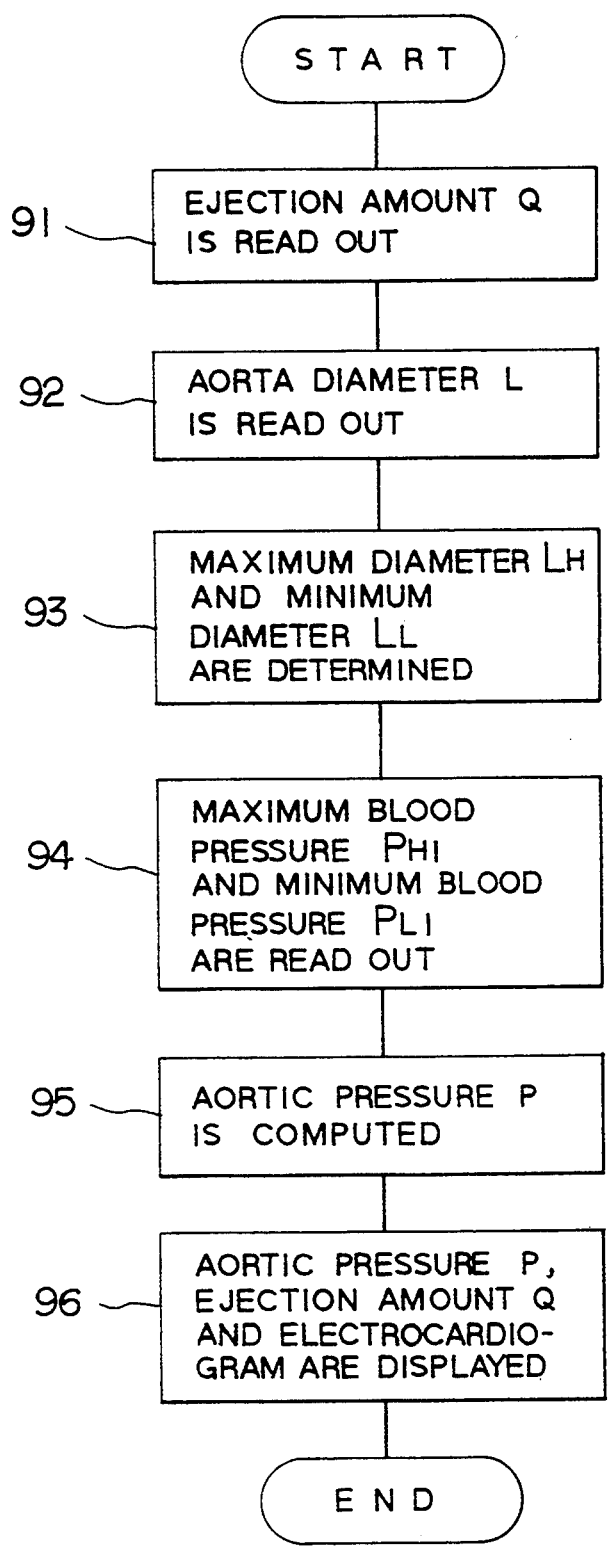
FIG. 7 illustrates an example of the process of computing the aorta pressure.

In computing and displaying the aortic pressure P, the data analyzing section 41 causes a program to be started which corresponds to the procedure illustrated in FIG. 7. In other words, the data regarding the ejection amount Q and the aortic diameter L, which were input at Steps 81 through 85 in FIG. 5, are read out respectively (Steps 91 and 92). Then, from the aortic diameter L data, the maximum value $L_H$ and the minimum value $L_L$ are determined (Step 93). After the maximum blood pressure $P_{H1}$ and the minimum blood pressure $P_{L1}$, which were input at the procedure in FIG. 3, have been read out (Step 94), the aortic pressure P is computed based on the formula (3) (Step 95). At this time, a proper value for each correction factor $\alpha_1$ and $\beta_1$ is previously set. The aortic pressure computed in Step 94 may be carried out based on the aforementioned formula (5) or (6) to obtain an approximate value.

Figure 8:
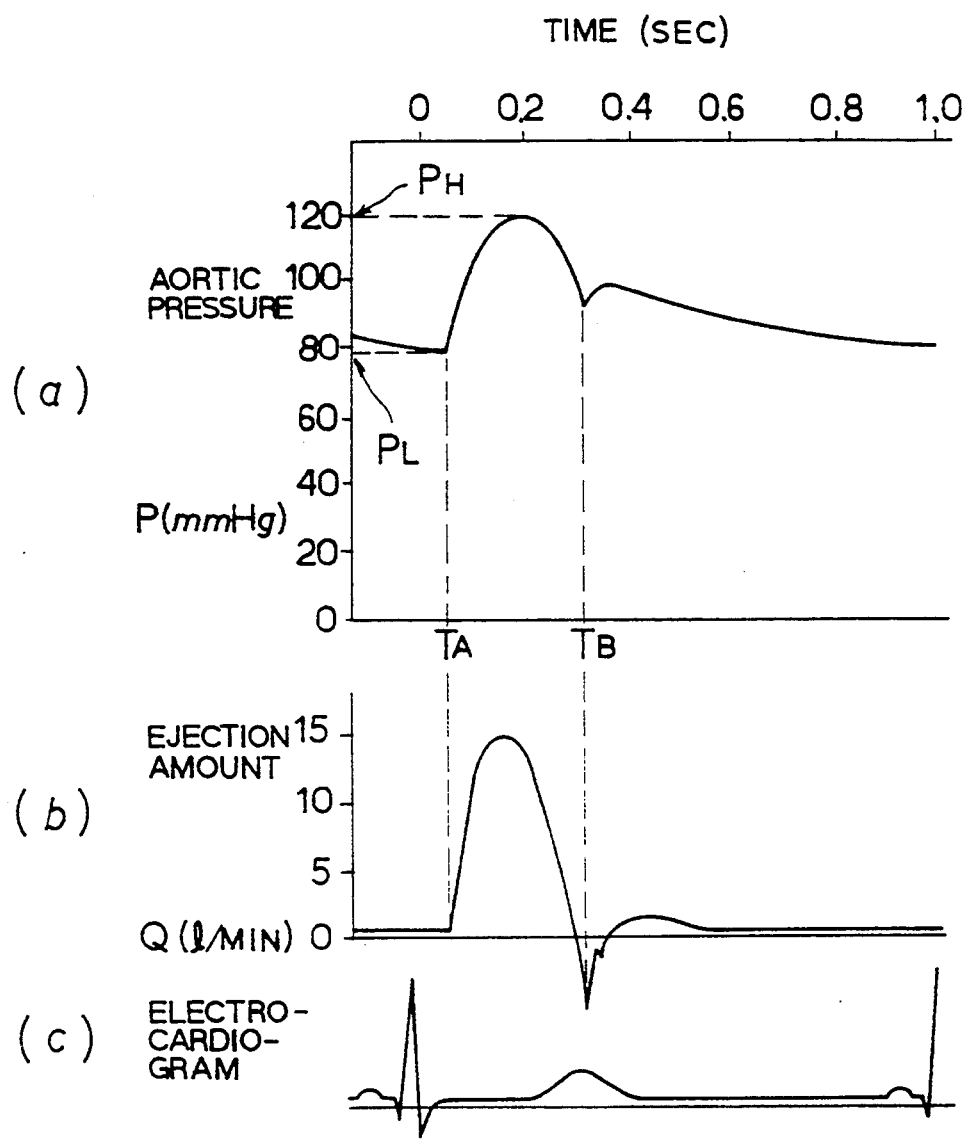
FIG. 8 shows graphs each illustrating respectively how the aorta pressure, the blood flow, and the electrocardiogram waveform change with time.

Finally, timing matching is carried out of the waveforms, based on the ECG signals, of the data regarding the aortic pressure P, the ejection amount Q, and the electrocardiogram. Then, this set of data are output to the DSC 27 and the recorder 53 (Step 96). As shown in FIG. 8, with time as the horizontal axis, this allows the aortic pressure P, the ejection amount Q and the electrocardiogram to be simultaneously displayed for one heart beat or plurality of heart beats, while the cardiac timings of the aortic pressure P, the ejection amount Q, and the electrocardiogram are matched.

A different parameter will be described for cardiac function analysis. Just as the ejection amount, the left ventricle volume (cardiac volume) is also an important parameter for cardiac function evaluation. This cardiac volume V is obtained from the ejection amount Q and the maximum ventricular volume $V_M$ or the ejection fraction EF.

The ejection fraction EF is represented as the ratio of the stroke volume SV to the cardiac volume at the end diastole. It is obtained by:

$$EF=SV/V_M \quad (7)$$

(where $V_M$ is the ventricular volume at the end diastole or the maximum ventricular volume.) When the ejection amount (instantaneous stroke volume) is defined as Q [l/min], the ejection volume for one heart beat, that is, the stroke volume SV is obtained by:

$$SV = \int_{T_A}^{T_B} Q dt \quad (8)$$

The cardiac volume V is the cardiac volume $V_M$ at the end diastole minus the ejection amount so that:

$$V = V_M - \int_{T_A}^{t} Q dt \quad (9)$$

Substituting (7) and (8) into (9) gives:

$$V = \left(\int_{T_A}^{T_B} Q dt\right)/EF - \int_{T_A}^{t} Q dt \quad (10)$$

Figure 4:
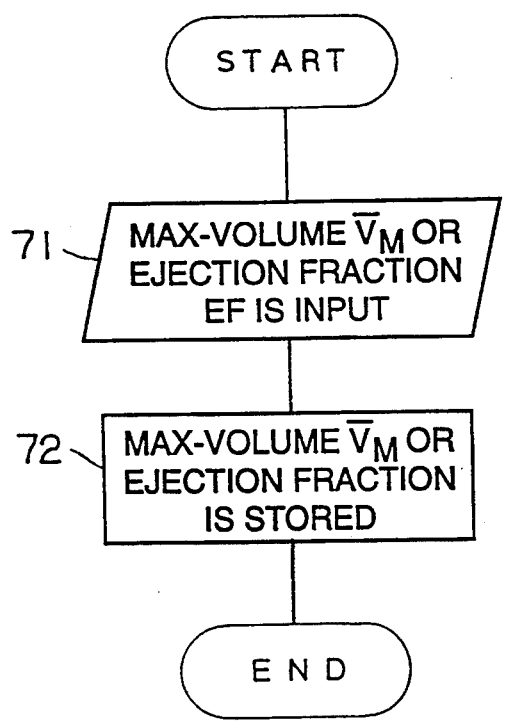
FIG. 4 is a flow chart illustrating an example of the process of incorporating ejection fraction.
Figure 9:
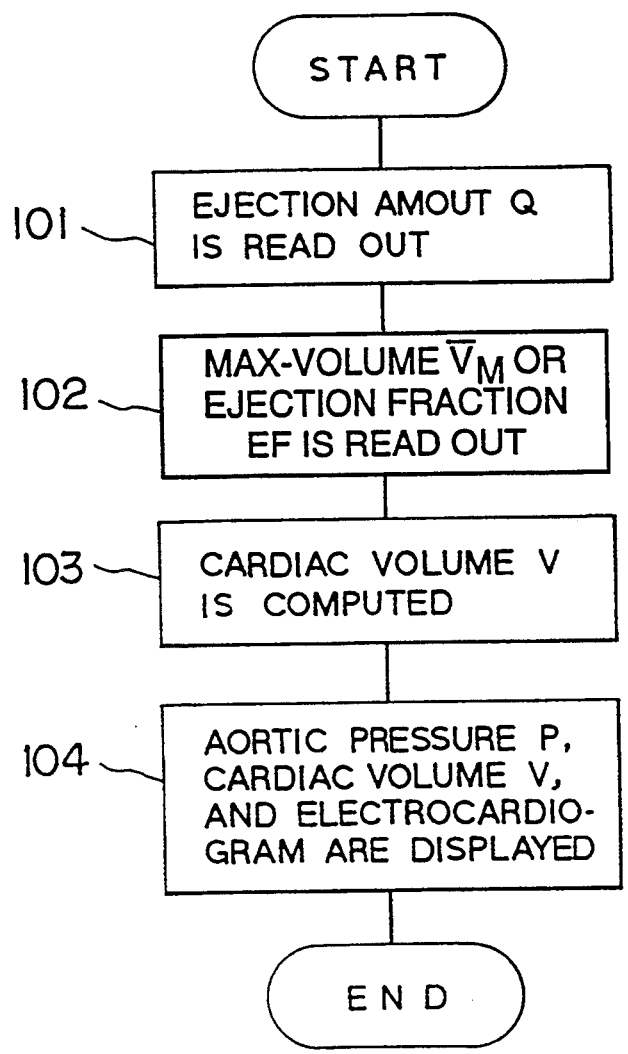
FIG. 9 is a flow chart illustrating an example of computing the cardiac volume.
Figure 10:
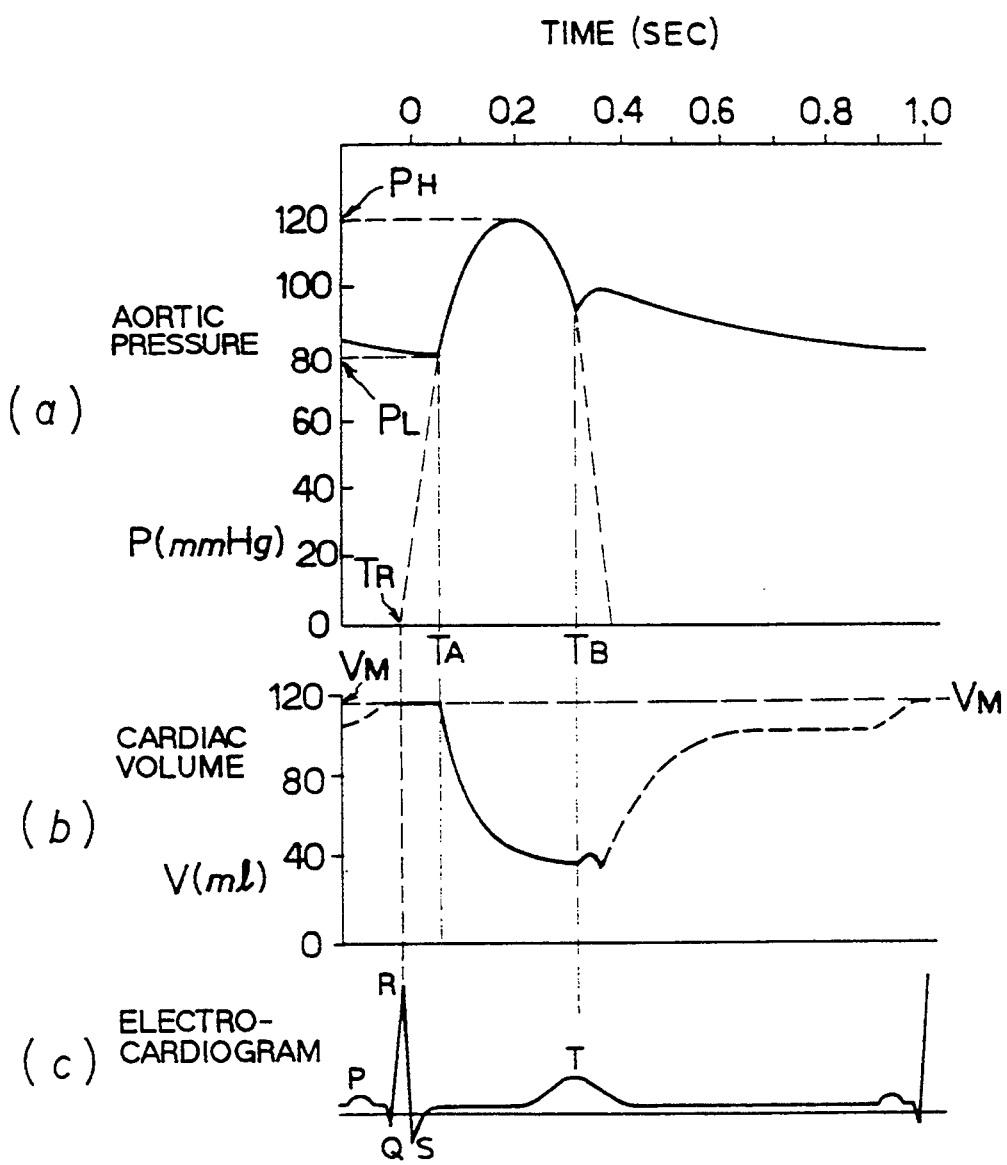
FIG. 10 shows graphs each illustrating respectively how the aorta pressure, the cardiac volume, and the electrocardiogram waveform change with time.

In computing and displaying the cardiac volume V, the data analyzing section 41 starts a program which corresponds to the procedure illustrated in FIG. 9. The data regarding the ejection amount Q (average value will do) for one heart beat, which was previously input, is read out (Step 101). Then, the maximum volume $V_M$ or the ejection rate EF data, which has been previously input in FIG. 4, is read out (Step 102). The cardiac volume V is computed based on the formula (9) or (10) (Step 103). The waveforms, based on the ECG signals, of the data regarding the aortic pressure P, the cardiac volume V, and the electrocardiogram are time-phased, which are output to the DSC 27 and the recorder 53 (Step 104). As shown in FIG. 10, with time as the horizontal axis, this allows those data for one heart beat or a plurality of heart beats to be simultaneously displayed, while the cardiac timings of the aortic pressure P, the cardiac volume V, and the electrocardiogram are matched.

As shown in FIG. 10(b), at time $T_A$ when the aortic valve opens, blood flows out from the ventricle, which reduces the cardiac volume. At time $T_B$ when the aortic valve closes, the heart expands, thereby gradually increasing the cardiac volume V to a maximum volume $V_M$ at the end diastole.

As a different parameter for cardiac function analysis, the relationship between the aortic pressure P and the cardiac volume V (aortic pressure—volume curve) can be computed. When the aortic valve is normal and opens sufficiently, the intercardiac pressure and the aortic pressure are almost equal so that the aortic pressure P may be substituted as the intercardiac pressure.

Figure 11:
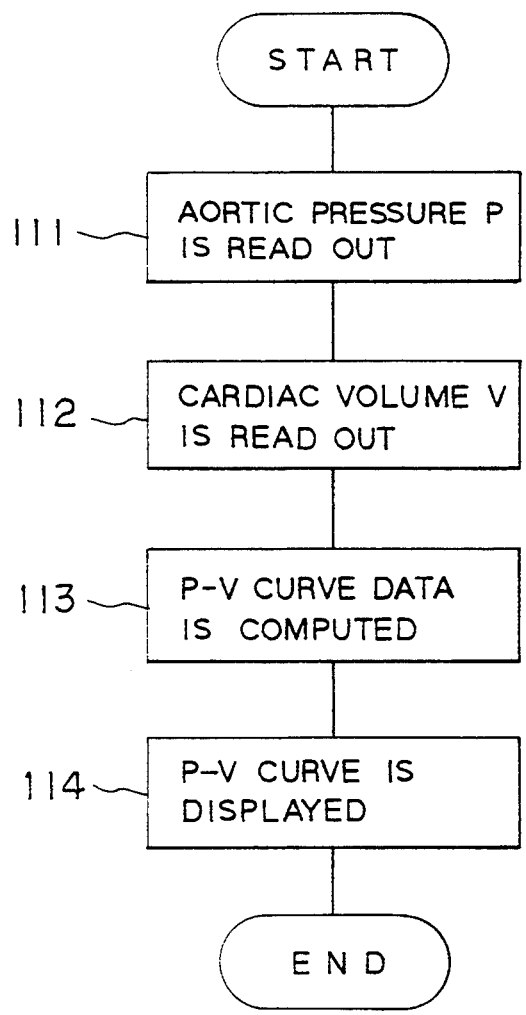
FIG. 11 is a flow chart of an example of computing the aorta pressure—cardiac volume data.
Figure 12:
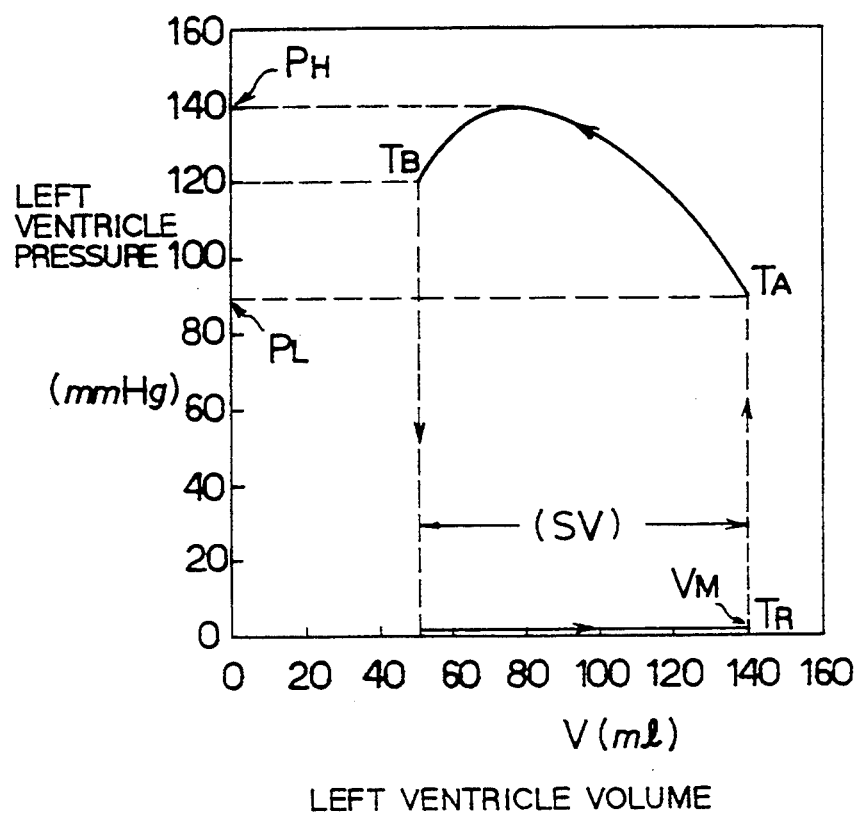
FIG. 12 is a two dimensional graph of the left ventricle pressure versus the left ventricle volume.

In estimating the aortic pressure—volume curve, the data analyzing section 41 executes a procedure illustrated in FIG. 11. In the procedure, data regarding the aortic pressure P and cardiac volume V for one heart beat are each read out from the memory to the work area (Steps 111 and 112). For the aortic pressure P and the cardiac volume V, the values obtained in FIGS. 9 and 10 can be used. The data regrading the aortic pressure—volume curve is generated based on the read-out P, V data (Step 113). The generated aortic pressure—volume curve data is output, for example, to the DSC 27 (Step 114). As shown in FIG. 12, this allows a graph of the aortic pressure P—volume V curve to be displayed, whereby changes in the internal pressure of the left ventricle can be alternatively estimated.

As can be seen from the P—V curve, the maximum value VM of the ventricle volume is obtained at the end diastole, with a small amount of blood flowing from the left atrium, the intercardiac pressure (left ventricle pressure) is almost zero. In FIG. 12, this value is zero. When the heart starts to contract, the intercardiac pressure rises while the volume is constant until the aortic valve opens. After the aortic valve has opened, while the intercardiac pressure rises further, blood flows out from the ventricle, thereby reducing the cardiac volume. The time period $T_A$ to $T_B$ is where the aortic pressure P—volume V curve can be obtained from the measured aorta diameter and the ejection amount (a continuous line in the graph). At the diastole, the aortic valve closes and the intercardiac pressure drops suddenly. Therefore, blood flows into the ventricle and the cardiac volume V increases to $V_M$.

The work done will be described as another parameter. The work done W (or work done required to send blood throughout the body) which the ventricle performs to the external world for one heart beat is represented by the area of the "pressure—volume" curve illustrated in FIG. 12. It is obtained by:

$$W = \oint PdV \tag{11}$$

Substituting $dV = -Qdt$ [from (10)] gives:

$$W = -\int_{T_B}^{T_A} Qdt = \int_{T_A}^{T_B} Qdt \tag{12}$$

Figure 13:
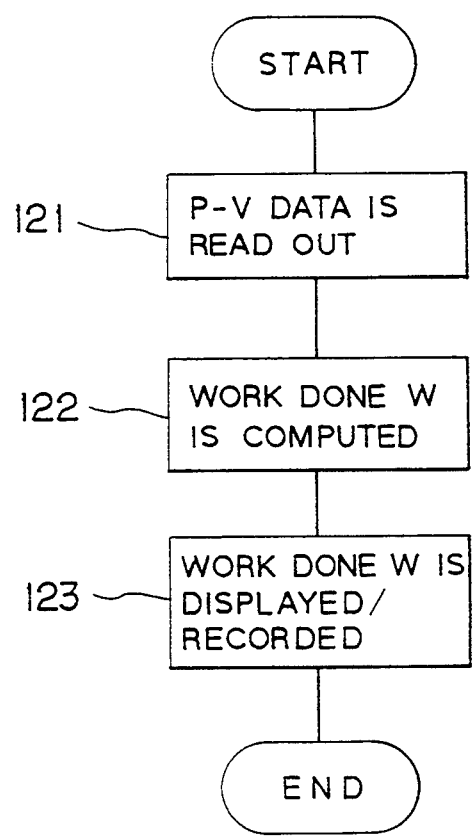
FIG. 13 is a flow chart of an example of computing the amount of work performed.

To obtain the work done W, the data analyzing section 41 executes the procedure illustrated in FIG. 13. First, the aortic pressure P—volume V curve data, which has been computed by the procedure of FIG. 11, is read out from the memory to the work area (Step 121). Then, the work done W is computed based on the formula (11) or (12) mentioned above, which is numerically displayed and recorded (Steps 122, 123).

The work done is displayed and recorded in the form of a graph in which the work done W or the value obtained by multiplying the number of heart beats to W is plotted against time. It is useful monitoring the condition of the patient during operation, or examining how much the patient's condition has worsened or improved.

Another index useful for cardiac function evaluation is the maximum rise rate of the left ventricle pressure 'peak dP/dt'. After the ventricle has started contracting, its pressure suddenly rises. The 'peak dP/dt' represents the maximum rate at which the pressure rises suddenly. The parameter 'peak dP/dt' may be approximately obtained by:

$$\text{peak } dP/dt \approx P_L/(T_A - T_R) \tag{13}$$

As shown in FIG. 10(a), TR is the time when the R-wave appears in the electrocardiogram. $T_A$ is the time when the aortic valve starts opening, and $T_R \sim T_A$ is the previous ejection period. $P_L$ represents the minimum blood pressure.

Figure 14:
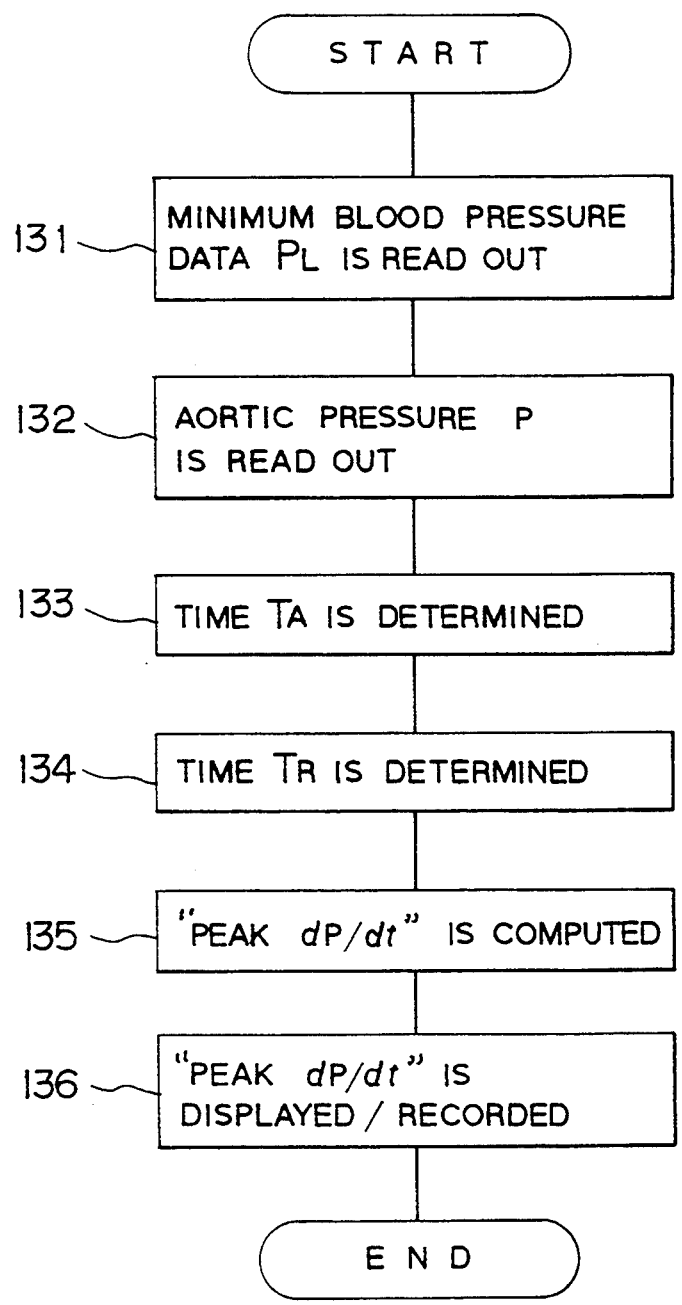
FIG. 14 is a flow chart of an example of computing the maximum rate of pressure rise of the left ventricle.

The maximum rise rate of the left ventricle pressure 'peak dP/dt' is computed and displayed by means of the procedure of FIG. 14 executed by the data analyzing section 41. First, the already stored data regarding the minimum blood pressure $P_L$ and the aortic pressure P are read out (Steps 131 and 132). Then, the time $T_A$ when the aortic valve starts opening is determined from the aortic pressure P data (Step 133). The time $T_R$ when the R-wave appears is determined from the read out waveform data of the electrocardiogram (Step 134). When these have been determined, the data analyzing section 41 computes the maximum rise rate of the left ventricle pressure 'peak dP/dt' according to formula (13), which is displayed and recorded (Steps 135, 136).

As described above, in the embodiment, the maximum blood pressure $P_H$ and the minimum blood pressure $P_L$ comprising a portion of the basic data are collected as data of spots. Then, the aortic diameter L and the ejection amount Q are, in real time, collected and displayed (see FIG. 6). Thereafter, a desired parameter is selected from any one of the aortic pressure P, the cardiac volume V, the "left ventricle pressure—left ventricle volume" curve, the work done W, and the maximum rise rate of the left ventricle pressure 'peak dP/dt'. The selected parameter is displayed.

Accordingly, the method, using ultrasonic pulses, allows cardiac function information to be obtained non-invasively, so that the patient is not burdened. This permits the patient to undergo examination without resistance to it. This in turn allows the operator to easily employ his equipment. Further, since the cardiac function information is displayed in a form suitable for examination, an overall cardiac function evaluation can be easily carried out, the diagnosis accuracy is improved, and the time required for evaluation is shortened.

In FIGS. 8 and 10, changes of the cardiac function parameters of aortic pressure P, ejection amount Q, and cardiac volume V are displayed based on the electrocardiogram waveforms, with their cardiac timings matched. With the timings matched, the basic data and plurality of parameters can be compared and a observed on the time axis.

In the embodiment, the basic data, themselves, can be successively and independently obtained. However, a method in which the ECG signal is simultaneously taken in from the electrocardiograph is adopted. In addition, in consideration of slightly-changed heart beat intervals, data regarding the average of the plurality of heart beats is used (see Step 85 of FIG. 5). This allows the time phases to be easily matched and stable processing to be performed based on average value data. Although instantaneous changes which occur, for example, with every heart beat cannot be measured, it is sufficiently useful for cardiac function evaluation.

Obviously, a construction which does not use data regarding the average of the plurality of heart beats may be used for the system. In addition, the construction may be such as to allow comparison and observation of the changes of data which occur with each heart beat and parameters.

The system may be so constructed as to allow simultaneous measurement of the aforementioned basic parameters (ejection amount Q, aorta diameter L, electrocardiogram) as another method for matching time phases. Simultaneous measurement is useful for examination during operation and for clinical purposes because automatic processing by the data analyzing section 41 can be easily carried out and data can be obtained every moment in real time.

In simultaneous measurement, different ultrasonic probes may be used for the ejection amount Q and the aorta diameter L respectively, and two processing circuits may be used for individually processing the signals detected by the two probes to output this processed signals to the data analyzing section. The construction described below in which a single probe is capable of being inserted into the esophagus is very convenient from the viewpoint of operability and cost.

Figure 15:
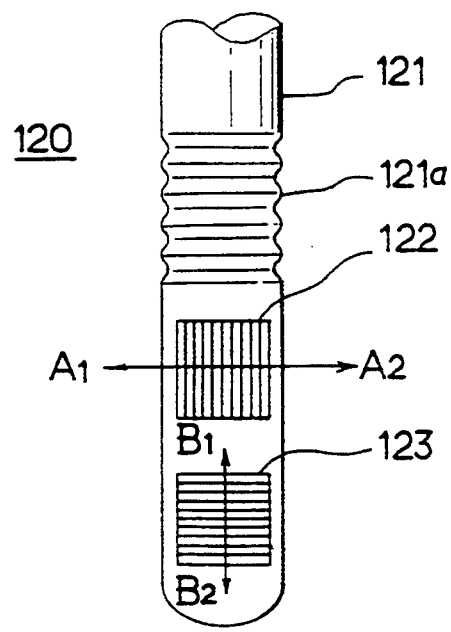
FIG. 15 is a partial view of one example of an esophagus-insertable ultrasonic probe.

Measurements using this kind of probe will be described with reference to FIGS. 15 and 16. FIG. 15 shows an example of an esophagus-insertable ultrasonic probe 120. The probe 120 has an introducing tube 121 which can be inserted into the esophagus, with the tube 121 having a bent section 121a. The front end of the introducing tube 121 has two pairs of array transducers 122 and 123.

Of these, in the first array transducers 122, elongated piezoelectric elements are arranged vertically in the axial direction of the introducing tube 121. Signals which are transmitted and received by means of the first array transducer 122 have their phases controlled, so that the A1-A2 surface is scanned in a direction perpendicular to the introducing tube 121 axis. In the second array transducer 123, elongated piezoelectric elements are in the same way disposed in the axial direction of the introducing tube 121. Then, the second array transducer 122 causes scanning of the B1-B2 surface in a direction parallel to the axis of the introducing tube 121. In the last analysis, it is possible to obtain a tomographic image of the A1-A2 surface, which is perpendicular to the axis, by means of the first array transducer 122. It is also possible to obtain a tomographic image of the B1-B2 surface, which is parallel to the axis, by means of the second array transducer 123.

Figure 16:
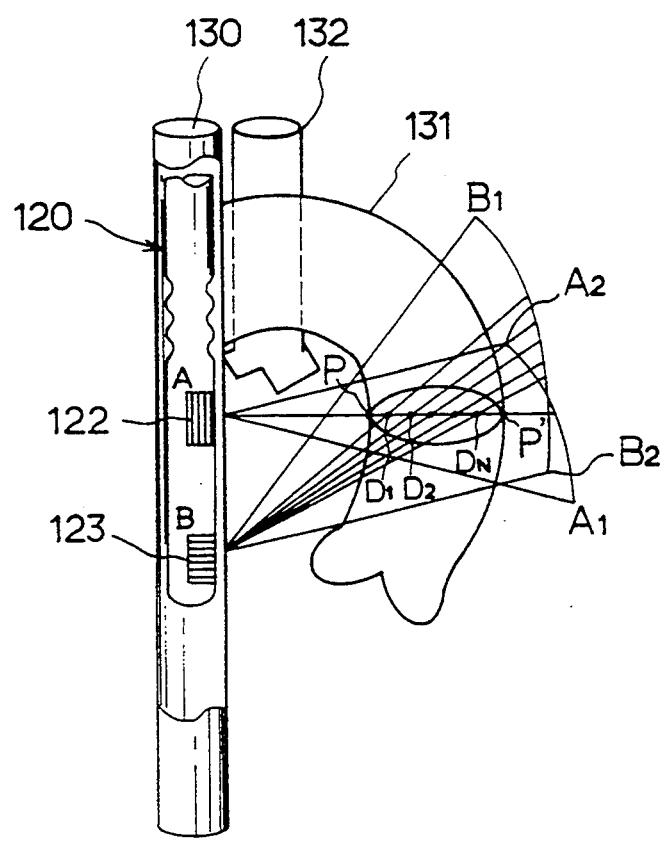
FIG. 16 is an explanatory view of the operation of an inserted esophagus-insertable ultrasonic probe.

FIG. 16 illustrates an example of an application of the esophagus-insertable ultrasonic probe 120 formed in this way. The ultrasonic probe 120 is inserted to where it faces an aorta 131 in the esophagus. There can be scanned simultaneously the cross section of the aorta 131 by means of the first array transducer 122 (see arc $A_1$–$A_2$) and the longitudinal section of the aorta 131 by means of the second array transducer 123 (see arc $B_1$–$B_2$). Reference numeral 132 denotes the trachea.

Based on the simultaneous scannings, the blood vessel diameter and the ejection amount are measured by known methods. Two points P and P' are set on the central line of the cross section which is perpendicular to the central axis of the aorta 131. The first array transducer 122 measures the distance P-P', or the diameter of the aorta. The second array transducer 123 measures beam direction components of flow velocities at the plurality of points $D_1, D_2, \ldots, D_n$ on the central line P-P'. The angles made by the ultrasonic beams which pass the points $D_1, D_2, \ldots, D_n$ and the central line P-P' are automatically obtained. Using those values, the flow amounts in the axial direction of the aorta 131 at the point $D_1, D_2, \ldots, D_n$ are each obtained. Annular cross section areas are multiplied by the flow amounts respectively, and the resulting values are added together to give the ejection amount value. In this way, changes in diameter and ejection amount of the longitudinal section and the cross section including the same central line P-P' can be measured at the same time. Based on these measured values, using the aforementioned method, various cardiac function parameters are computed and output/displayed. At this time, the electrocardiogram is measured at the same time, and parameters are computed and displayed in the same way as described above.

The measurement of the aorta, itself, was used to describe the aforementioned embodiment. Another method may be used to obtain approximate values. In this method, the probe is placed against the common carotid artery (thick artery), which is easier to place against than the chest section, to measure its diameter in the same way and to compute the various parameters based on this measured value.

In the aforementioned embodiment, various parameters which represent cardiac function have been described. Obviously, a desired parameter alone may be measured, computed, and displayed.

In addition, the overall ultrasonic cardiac examination system is made smaller in size and simplified by constructing it so that common use may be made of the ultrasonic transmission and reception circuit portion. In measuring the ejection amount, the ejection fraction, and the blood vessel diameter, separate ultrasonic transmission/reception circuits which include an ultrasonic probe may be provided, when necessary.

The construction using ultrasonic pulses to measure the ejection fraction has been described. The ejection fraction, however, can also be measured based an anglographic data obtained by measuring the anglographic image based on X-rays or nuclear medicine.

Accordingly, in the present invention, basic cardiac function data which are directly measured (ejection amount, blood vessel diameter, blood pressures, and/or ejection fraction, and/or electrocardiogram signals) is used to estimate and compute the various cardiac function parameters, which are displayed in an optimal form. This allows information regarding the body interior to be detected by a simple method of measurement based on ultrasonic pulses. This method allows examination non-invasively, and provides various cardiac information in a form which shows how it changes with time, which is useful for diagnosing the patient and excellent in reproducibility.

Since the proper cardiac function information can be obtained at the right time, the patient can be properly cured with an accurate understanding of the patient's heart condition. In particular, the system is extremely useful for observing the condition of the patient during operation. By recording the cardiac function information (basic data and computed parameters) or graph, the condition of the patient can be known for different time phases.

The system is constructed to make detections using ultrasonic pulses, so that compared to conventional systems it is partly improved, with additional functions. It is low in cost and requires less space, so that it is a highly practical system.

In addition, since the examination can be performed noninvasively, the patient will not have to worry and be mentally burdened before the examination. At the same time, the operator can easily carry out the operation of the system without much trouble.

What is claimed is:

1. A system for examining a cardiac function comprising:
   means for measuring a blood flow amount ejected from a ventricle of a heart to an aorta of an object using reflected wave information of an ultrasonic pulse;
   means for measuring a blood vessel diameter of either one of the aorta and a thick artery using reflected wave information of another ultrasonic pulse;
   means for inputting, as a blood pressure data, at least one of a maximum and a minimum blood pressures; and
   means for acquiring a parameter concerning the cardiac function on the basis of the measured ejection amount, the measured blood vessel diameter and the inputted blood pressure data.

2. The system according to claim 1, wherein said thick artery is either one of a common carotid artery and a brachial artery.

3. The system according to claim 1, wherein said parameter acquiring means comprises means for calculating the parameter and means for displaying the parameter calculated by the parameter calculating means.

4. The system according to claim 3, wherein said parameter is a time-varying data of the blood pressure of either one of the aorta and the thick artery and said parameter calculating means is a means that calculates the time-varying data on the basis of the measured blood vessel diameter and the inputted blood pressure data.

5. A system for examining a cardiac function comprising:
  means for measuring a blood flow amount ejected from a ventricle of a heart to an aorta of an object using reflected wave information of an ultrasonic pulse;
  means for measuring a blood vessel diameter of either one of the aorta and a thick artery using reflected wave information of another ultrasonic pulse;
  means for measuring either one of a maximum volume and an ejection function of a left ventricle of the heart;
  means for inputting, as a blood pressure data, at least one of a maximum and a minimum blood pressures; and
  means for acquiring a parameter concerning the cardiac function on the basis the measured ejection amount, the measured blood vessel diameter, the measured one of the maximum ventricular volume and the ejection function and the inputted blood pressure data.

6. The system according to claim 5, wherein said ejection fraction measuring means is a means that measures either one of a maximum volume and the ejection fraction using information of a reflected ultrasonic pulse wave from the heart.

7. The system according to claim 5, wherein said thick artery is either one of a common carotid artery and a brachial artery both connected to the heart.

8. The system according to claim 5, wherein said parameter acquiring means comprises means for calculating the parameter and means for displaying the parameter calculated by the parameter calculating means.

9. The system according to claim 8, wherein said parameter is a time-varying data of the blood pressure of either one of the aorta and the thick artery and said parameter calculating means is a means that calculates the time-varying data on the basis of the measured blood vessel diameter and the inputted blood pressure data.

10. The system according to claim 9, wherein said blood pressure inputting means is means for inputting a value read out from a sphygmomanometer using a cuff and said parameter calculating means includes means for correcting the inputted readout value and obtaining the time-varying data of the blood pressure.

11. The system according to claim 9, further comprising means for measuring an electrocardiogram wave of the heart, wherein said parameter displaying means is means that displays simultaneously both time-depending data of the measured ejection amount and the measured electrocardiogram wave both set to be coincident with each other in a cardiac timing based on the measured electrocardiogram wave.

12. The system according to claim 8, wherein said parameter is a time-varying data of a volume of the left ventricle and said parameter calculating means is means that calculates the time-varying data of the volume on the basis of the measured ejection amount and the measured ventricular volume or ejection fraction.

13. The system according to claim 12, further comprising means for measuring an electrocardiogram wave of the heart, wherein said parameter displaying means is means that displays simultaneously all time-depending data of the measured ejection amount, the calculated parameter, and the measured electrocardiogram wave all set to be coincident with each other in a cardiac timing based on the measured electrocardiogram.

14. The system according to claim 8, wherein said parameter is time-varying data consisting of the blood pressure of either one of the aorta and the thick artery and a volume of the left ventricle, said parameter calculating means is means that calculates the time-varying data on the basis of the measured blood vessel diameter, the measured ejection amount, the measured one of the maximum ventricular volume and the ejection fraction and the inputted blood pressure data, and said parameter displaying means displays the calculated parameter as a two-dimensional image whose horizontal and vertical axes are assigned to the volume and the blood pressure, respectively.

15. The system according to claim 8, wherein said parameter is work done of the left ventricle and said parameter calculating means is means that calculates the work done on the basis of the measured blood vessel diameter, the measured ejection amount, the measured one of the maximum ventricular volume and the ejection fraction and the inputted blood pressure data.

16. The system according to claim 8, wherein said parameter is a ratio of a rise blood pressure versus a period from an appearance time of an R-wave on an electrocardiogram to a rise time of a blood pressure of either one of the aorta and the thick artery.

17. The system according to claim 5, further comprising means for measuring an electrocardiogram wave of the heart in parallel with the measurements of the ejection blood flow amount measuring means and the blood vessel diameter measuring means.

18. The system according to claim 17, further comprising means for simultaneously displaying, as a basic data, a time-depending data of the measured ejection amount, the measured blood vessel diameter and the measured electrocardiogram wave all set to be coincident with each other in a cardiac timing based on the measured electrocardiogram wave.

19. The system according to claim 5, wherein an esophagus-insertable ultrasonic probe is provided to transmit and receive said ultrasonic pulse.

20. The system according to claim 19, wherein said esophagus-insertable ultrasonic probe includes two transducers simultaneously driven and wherein said ejection amount measuring means is means that uses one of the two transducers and said blood vessel diameter measuring means is means that uses a remaining one of the two transducers.

21. The system according to claim 20, wherein each of said two transducers is a phased-array-type transducer having a scanning plane for the ultrasonic pulse, each of the scanning plane of the two transducers are approximately perpendicular to each other.

22. A system for examining a cardiac function comprising:

means for measuring a blood vessel diameter of either one of an aorta and a thick artery of an object using reflected wave information of an ultrasonic pulse;

means for inputting, as a blood pressure data, a maximum and a minimum blood pressures of the object; and means for acquiring a parameter concerning a time variation in an absolute value of either one of an aorta pressure and the blood pressure.

23. A system for examining a cardiac function comprising:

means for measuring an amount of a flood flow ejected from a ventricle of a heart to an aorta of an object using a reflected wave information of an ultrasonic pulse;

means for measuring either one of a maximum volume and an ejection fraction of a left ventricle of the heart using a reflected wave information of another ultrasonic pulse; and means for acquiring a parameter concerning an absolute value of a cardiac volume of the heart and a time variation of the absolute value on the basis of the measured ejection amount and the measured one of the maximum volume and the ejection fraction.

* * * * *

UNITED STATES PATENT AND TRADEMARK OFFICE
CERTIFICATE OF CORRECTION

PATENT NO. : 5,450,850
DATED : September 19, 1995
INVENTOR(S) : Kazuhiro IINUMA

It is certified that error appears in the above-indentified patent and that said Letters Patent is hereby corrected as shown below:

Column 9, line 1, delete "-" after "(";

line 10, delete "-" after "$P_{L1}$";

line 14, insert --$\alpha$-- after "for".

Signed and Sealed this

Twenty-first Day of May, 1996

Attest:

BRUCE LEHMAN

Attesting Officer     Commissioner of Patents and Trademarks